United States Patent [19]

Gusterson et al.

[11] Patent Number: 6,051,221

[45] Date of Patent: Apr. 18, 2000

[54] BRK PROTEIN TYROSINE KINASE AND ENCODING NUCLEIC ACID

[75] Inventors: Barry Austin Gusterson, Greater London; Mark Roger Crompton, London; Philip John Mitchell; Karen Tracey Barker, both of Sutton; Taherah Kamalati, London; Martin John Page, Biggin Hill, all of United Kingdom; Paul Spence, Newtown, Pa.

[73] Assignee: Glaxo Wellcome Inc., Research Triangle Park, N.C.

[21] Appl. No.: 08/591,474

[22] PCT Filed: Jul. 8, 1994

[86] PCT No.: PCT/GB94/01479

§ 371 Date: Jun. 10, 1996

§ 102(e) Date: Jun. 10, 1996

[87] PCT Pub. No.: WO95/02057

PCT Pub. Date: Jan. 19, 1995

[30] Foreign Application Priority Data

Jul. 9, 1993 [GB] United Kingdom .................. 9314233
Mar. 11, 1994 [GB] United Kingdom .................. 9404817

[51] Int. Cl.[7] .................. A61K 38/43; C12N 15/12; C12N 15/11; C12N 5/10

[52] U.S. Cl. .................. 424/94.3; 424/94.1; 435/69.1; 435/320.1; 435/325; 435/252.3; 435/254.11; 530/300; 530/350; 536/23.1; 536/23.2; 536/23.5

[58] Field of Search .................. 435/69.1, 325, 435/320.1, 252.3, 254.11; 536/23.5, 23.1, 23.2; 530/350, 300; 574/2

[56] References Cited

U.S. PATENT DOCUMENTS 5,480,968  1/1996  Kraus et al. .................. 530/326

OTHER PUBLICATIONS

Stephens et al Lance vol. 2(8192): pp. 435–438 Aug. 30, 1997.

*Primary Examiner*—Lorraine Spector
*Assistant Examiner*—Claire M. Kaufman
*Attorney, Agent, or Firm*—Nixon & Vanderhye P.C.

[57] ABSTRACT

The invention relates to a novel tyrosine kinase designated brk and the use of this tyrosine kinase in the development of diagnostic and therapeutic approaches to cancer. The novel tyrosine kinase was isolated from a human metastatic breast tumor using a PCR based differential screening approach and has the deduced amino acid sequence shown in SEQ ID NO:2.

25 Claims, 3 Drawing Sheets

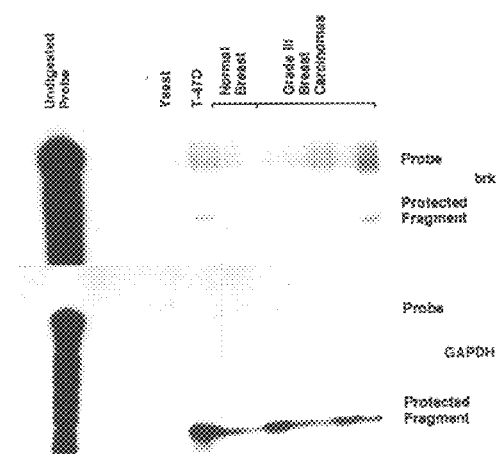
Fig. 4
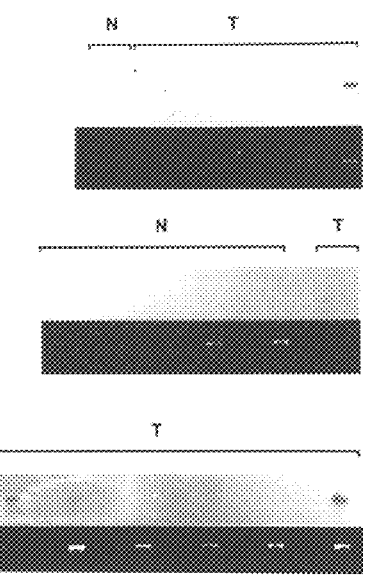
Fig. 5A
Fig. 5B
Fig. 5C

BRK PROTEIN TYROSINE KINASE AND ENCODING NUCLEIC ACID

FIELD OF THE INVENTION

The present invention relates to a putative signalling molecule. More particularly the invention relates to a novel tyrosine kinase and the use of this tyrosine kinase in the development of diagnostic and therapeutic approaches to cancer, for example breast cancer.

BACKGROUND OF THE INVENTION

Protein tyrosine kinases are enzymes which show the property of catalysing the transfer of phosphate groups from donor molecules (ATP) to the hydroxyl groups of tyrosine residues in polypeptides. Known tyrosine kinases can be classified into two broad groups. Transmembrane tyrosine kinases traverse cellular membranes so that they possess extracellular and intracellular domains. Cytoplasmic tyrosine kinases are located only intracellularly. A general feature of transmembrane (also referred to as receptor) tyrosine kinases is that they possess extracellular ligand-binding domains, hydrophobic transmembrane sequences, and intracellular portions which include the tyrosine kinase domains (for a review see Ullrich & Schlessinger Cell, 61, 203–212 (1990)).

Tyrosine kinases can induce cell proliferation, cell transformation and regulate developmental events (see reviews by Hanks et al, Science, 241, 42–75 (1988) and Cantley et al, Cell 64, 281–302 (1991)). In general, where functional assays have been available (e.g. mitogenesis or transformation), it has been shown that the biological functions of tyrosine kinases are usually dependent on intact enzyme activity and that through autophosphorylation and the phosphorylation of other proteins, they alter the subcellular localisation and activities of various components of the intracellular signalling pathways.

Analysis of the oncogenes of many acutely transforming animal retroviruses has revealed that their products frequently manifest tyrosine kinase activity, as do the products of their cellular proto-oncogene counterparts. Other genes encoding tyrosine kinases have been found to be altered by DNA rearrangements in cancer cells, the result being a presumed acquisition of cellular transforming activity (for example c-abl, c-met). Some cellular proto-oncogenes encoding tyrosine kinases have been cloned independently by virtue of the fact that they encode growth factor receptors, for example the epidermal growth factor receptor. On the other hand, the genes for other growth factor receptors which have tyrosine kinase activities, such as those for platelet-derived growth factor and insulin-like growth factors, have been well characterised, but have never been found to be transduced by retroviruses.

The c-erbB-2/HER2/c-neu gene encodes a transmembrane receptor-like tyrosine kinase which is structurally very similar to the EGF/TGF alpha receptor. The c-erbB-2 gene has been found to be overexpressed in 20 to 30% of human breast tumours, often in association with gene amplification, and this phenotype is now generally accepted as predictive of poor disease free and overall survival (for reviews see Sunderland & McGuire in Regulatory Mechanisms in Breast Cancer, Lippman & Dickson (Eds.), Kluwer Academic Publishers, Boston, pages 3 to 22 (1991) and Gusterson et al., J. Clin. Oncol., 10, 1049–1056 (1992)). Overexpression of the gene in fibroblasts induces transformation (di Fiore et al, Science, 237, 178–182 (1987) and Hudziak et al, Proc. Natl. Acad. Sci. (USA), 84, 7159–7162 (1987)), and ligands which bind to the c-erbB-2 gene product (human and rodent) and activate its tyrosine kinase activity have been identified (Lupu et al, Science, 249, 1552–1555 (1990), Dobashi et al, Proc. Natl. Acad, Sci. (USA), 88, 8582–8586 (1991), Wen et al, Cell, 69, 559–572 (1992) and Holmes et al, Science 256, 1205–1210 (1992)). Some of these ligands increase the rate of proliferation of cells expressing the c-erbB-2 protein. The strong implication of these and other findings is that overexpression of this tyrosine kinase in some breast tumour cells is one of the important steps in their progression towards tumourigenicity, and therefore that c-erbB-2 can function as an oncogene.

A variety of other receptor tyrosine kinases, including those for the IGFs and the FGFs, are expressed in breast tumours (Stewart et al, J. Biol. Chem., 265 21172–21178 (1990) and Wellstein & Lippman in Molecular Foundations of Oncology, Broder (Ed.), Williams and Wilkins, Baltimore, pages 403–418 (1991)), and the EGF/TGF alpha receptor is overexpressed in some cases (for example Horak et al, Oncogene, 6, 2277–2284 (1991)). As with c-erbB-2, overexpression of EGFr has been correlated with poor prognosis. Since the ligands of some of these receptors can be detected in breast tumour samples, it may be that breast tumour development is also regulated by these molecules (for a review see van de Vijver & Nusse, Biochim, Biophys. Acta, 1072, 35–50 (1991)).

The features which are ideally required in a molecular target for tumour therapies include preferential expression in the tumours, a role in the development of the tumours (rather than merely being a marker), and a knowledge of the mechanism of its action as a starting point for the rational design of activity modulators. It appears that all of these three criteria are satisfied, at least to some extent, in the case of c-erbB-2 and breast cancer and a considerable research effort is currently being directed to this molecule.

It has recently been found that the alkaloid K252a, at appropriate concentrations, selectively inhibits the tyrosine kinase and biological activities of the trk-class of neurotrophin receptors, but has no effect on the activities of v-src, v-fms or the receptors for EGF and PDGrF, and also does not affect general cell viability or proliferation (Tapley et al, Oncogene, 7, 371–381 (1992)). Members of another class of molecules, the tyrphostins, may be selective inhibitors of the EGFr/c-erbB-2 class of tyrosine kinases (Gazit et al, J. Med. Chem., 34, 1896–1907 (1991)). An antibody which inhibits the proliferation of human tumour cells by binding to the c-rbB-2 protein is currently uder evaluation as a potential cancer therapy (Carter et al, Proc. Natl. Acad. Sci. (USA), 89, 4285–4289 (1992))

If the transformation of a significant minority of breast tumour cells is due, at least in part, to the disregulated activity of the c-erbB-2 tyrosine kinase, then it seems likely that other breast tumours owe aspects of their transformed phenotype to the activity of other tyrosine kinases. The identification of further tumour associated tyrosine kinases would allow the development of novel diagnostic and therapeutic approaches to cancer and in particular breast tumours.

SUMMARY OF THE INVENTION

An object of the present invention is to provide a novel tyrosine kinase and its use in the diagnosis and/or therapy of cancer, particularly human breast tumours.

The present invention provides a DNA isolate encoding a novel protein tyrosine kinase or a fragment thereof, the protein tyrosine kinase being characterised by the amino acid sequence shown in SEQ ID NO. 2 or by an amino acid sequence showing a degree of homology thereto which is at least 60% in the catalytic domain and at least 40% in the remainder of the molecule, more preferably at least 90% overall, for example at least 95%.

According to one embodiment, the DNA isolate encodes the full amino acid sequence of the novel protein tyrosine kinase or an amino acid sequence showing a degree of homology thereto as defined above. According to another embodiment the DNA isolate encodes a fragment of the amino acid sequence of the protein tyrosine kinase or an amino acid sequence showing a degree of homology thereto as defined above. DNA sequence encoding fragments of the protein tyrosine kinase preferably encodes those parts of the amino acid sequence which characterise the enzyme, i.e. those parts which are most distinct from other protein tyrosine kinases.

The DNA sequence and deduced amino acid sequence of the novel protein tyrosine kinase are shown in SEQ ID NO. 1. most preferably the DNA sequence encodes all or part of the catalytic domain of the enzyme. The catalytic domain is encoded by nucleotides 617–1324 of SEQ ID NO. 1.

The DNA isolate may have the base sequence defined in SEQ ID NO. 1 to encode the relevant amino acid sequence. Alternatively the DNA isolate may have any other DNA sequence encoding the relevant amino acid sequence.

According to another embodiment, the invention provides a DNA isolate encoding amino acids 1 to 77 of SEQ ID NO. 2 followed by the amino acids of SEQ ID NO. 12. This coding sequence of this isolate may have the base sequence of nucleotides 29 to 552 inclusive of SEQ ID NO. 1, but excluding nucleotides 259 to 380 inclusive, or any other base sequence encoding the relevant amino acid sequence.

The present invention also provides a DNA isolate in the form of a cloning vector or an expression vector preferably a plasmid vector, including DNA as defined above. In the case of an expression vector the DNA will be under control of an appropriate promoter and will include regulatory elements required for expression in a suitable host cell.

The present invention also includes a recombinant cell line transformed with an expression vector as defined above and capable of expressing a recombinant protein tyrosine kinase or a fragment thereof characterised by the amino acid sequence shown in SEQ ID NO. 2 or an amino acid sequence showing a degree of homology thereto as defined above. Suitable host cells include mammalian cells, insect cells, yeast cells and bacterial cells and the expression vector will include a promoter and other regulatory elements appropriate to the host cell in question. Preferred host cells include CHO cells, myeloma cells, immortalised human breast cells, rodent fibroblast cell lines, baculovirus cells, yeast and *E. coli* cells. General techniques for manipulating DNA coding sequences and expressing such sequences in various types of cells are well known to those skilled in the art and are described for example in Sambrook et al, molecular Cloning: A Laboratory Manual, 2nd edition, Cold Spring Harbor Laboratory.

The present invention also provides a protein tyrosine kinase or a fragment thereof characterised by the amino acid sequence shown in SEQ ID NO. 2 or an amino acid sequence showing a degree of homology thereto as defined above.

The protein tyrosine kinase or a fragment thereof may be a recombinant polypeptide produced as the expression product of a coding sequence as defined above in a recombinant cell line. Alternatively the protein tyrosine kinase may be produced in a human tumour cell line. In either case the protein may be extracted and purified by standard techniques, for example antibody affinity chromatography. The glycosylation of the protein (if any) will depend on the cells in which it is produced and protein produced in human tumour cells in culture should have glycosylation equivalent to that produced in vivo in human tumours.

The DNA sequence set out in SEQ ID NO. 1 represents DNA sequence and deduced amino acid sequence from a novel tumour protein tyrosine kinases.

The DNA sequences encoding the novel protein tyrosine kinase has been isolated in the manner described in more detail in the example set out below but which involves briefly the following steps:

i) isolation of mRNA from metastatic tumour tissue;
ii) preparation of cDNA from the isolated mRNA;
iii) PCR amplification using degenerate oligonucleotide primers designed to amplify sequence associated with protein tyrosine kinases;
iv) subcloning PCR products;
v) identification of protein tyrosine kinase products amplified at higher levels from tumour bearing tissue;
vi) DNA sequencing and identification of novel protein tyrosine kinase sequence;
vii) isolation of the putatively full length cDNA from a cDNA library.

Application of the above protocol identified the above novel protein tyrosine kinase. The enzyme, which is believed to be a cytoplasmic tyrosine kinase, has been found to be overexpressed in certain human breast tumours as compared to normal breast tissue but has not been detected at all in other types of human tissue.

The present invention also relates to the application of the novel tyrosine kinase for the development of therapeutic, prognostic and diagnostic approaches to cancer. The invention is particularly applicable to breast cancer, however, the same approaches may also be applicable to other cancers and research data suggests a connection between breast cancer and ovarian cancer and also between these two cancers and gastric cancer.

In terms of therapy, the involvement of the novel tyrosine kinase in tumours means that beneficial clinical effects in the treatment of tumours can be obtained by modulating the tyrosine kinase activity and/or the functionality of the signalling molecule. There are a number of ways in which such modulation could be achieved.

The activity of the protein tyrosine kinase could be significantly impaired or inhibited by small chemical molecules and screens to identify suitable small molecular weight inhibitors can be developed in more detail below. This approach is analogous to that proposed for other tyrosine kinases (see "Drugs of the Future", 17(2), 119–131, (1992)). A further embodiment of this approach would be to derive nmr spectra or crystal structures for the protein tyrosine kinases or domains thereof and use the structural information so obtained to synthesise chemical structures de novo which could be similarly screened for activity as inhibitors.

The approach described above could be extended to encompass small peptides which are either competitive for signalling action of the tyrosine kinase, or which demonstrate useful binding thereto, such that its function is inhibited. This would include, for example, peptides which are capable of blocking substrate binding to the signalling molecule, including but not limited to those which bear SH2 domains. An additional approach is to use small molecules or peptides to block or interfere with ligand activation or dimerisation of the tyrosine kinase. Both of these events are generally required to effect a biological signal so that blocking or inhibition thereof could be used to therapeutic effect.

Protein tyrosine kinase function could also be blocked by expressing or administering a peptide which is a truncated or altered version of the protein. These are typically referred to as dominant negative proteins and are believed to sequester the active protein in a non-functional complex. Protein tyrosine kinase function could also be modulated by blocking translation of the mRNA encoding the protein using antisense oligonucleotides.

A further regulatory role of the protein tyrosine kinase could be manipulated by controlling expression or activity of specific phosphatases which control the degree of protein phosphorylation. It is recognised that the phosphorylation of specific residues, particularly tyrosine, threonine and serine residues, play an important role in transmitting a biological signal from the tyrosine kinase.

Use of the above therapeutic approaches depends on the identification and/or development of suitable agents for modulating, for example inhibiting, particular functions or activities of the protein tyrosine kinase. The present invention also relates to assays or screens by which such agents can be identified.

The present invention also provides a method of screening a substance for potential utility as a therapeutic agent in the treatment of cancer, in particular breast cancer, which comprises providing a standard system in which a protein tyrosine kinase as defined above or an active fragment thereof is able to develop a measurable effect, allowing the protein tyrosine kinase to develop that effect in the presence and absence of the said substance and measuring that effect, ability to produce significant inhibition of the effect being taken as an indication of potential utility as a therapeutic agent.

In accordance with this general principle, screens for potential therapeutic agents can take a number of forms. For example an initial screen to determine whether or not a substance merits further investigation as a potential inhibitor of the protein tyrosine kinase will usually be biochemical and should preferably be simple, rapid and capable of high through-put. Such screens will often make use of the protein expressed in a recombinant or derived from a cellular source in which the protein is over expressed. Particularly suitable recombinant expression systems include insect baculovirus, and the use of immortalised human breast cell lines or rodent fibroblast cell lines as host cells. The protein is then used directly in an in vitro assay with and without the potential inhibitor. This gives rapid data on the performance of the substance as an inhibitor often providing direct evidence that the substance can inhibit the enzymic activity of the protein tyrosine kinase and thus merits further study. This type of isolated system can also provide data on specificity but will not generally provide any information on bioavailability. The enzyme activity of the protein tyrosine kinase in vitro can be measured, for example, by measuring autophosphorylation or phosphorylation of a model substrate, by following incorporation of radioactive phosphate or by using anti-phosphotyrosine antibodies.

Further information concerning potential inhibitors can be provided by cell based screens which make use of a phenotypic alteration, e.g. a change in morphology and/or tumorigenicity, conferred by expression of the protein tyrosine kinase in a recombinant cell line or over-expression in any other available cell line. Particularly suitable recombinant cell lines again use immortalised human breast cell lines or rodent fibroblast cell lines as host cells. The cells can be used in proliferation or tumorigenicity assays with and without the potential inhibitor looking for substances able to halt growth of and/or morphologically detransform the cells. A control for substances which are generally cytotoxic can be provided by the same parental cell line engineered to express another oncogene which transforms the cells at a signalling point downstream of the protein tyrosine kinase. Assays of this sort can be very informative and they may provide data on mode of action of inhibitors.

The final stage of screening is the development of animal screens. These are time consuming and expensive and for these and ethical reasons their use is kept to a minimum, however they can give vital information regarding metabolism, clearance and performance of a substance in a true in vivo system which cannot be obtained in other ways. Animal screens ideally use the same recombinant or other cell lines as described above which express the protein tyrosine kinase. The cells are used as xenografts in animals, for example, nude mice, to give tumours whose growth is controlled by expression of the protein tyrosine kinase. The mice are then given inhibitors to determine whether they are capable of causing the selective regression of the xenografts without blocking the growth of a control xenograft. Alternatively transgenic animals which develop tumours by virtue of the appropriate tissue specific expression of the target protein tyrosine kinase can be used in a similar manner.

The invention also extends to therapeutic agents identified by use of any or all of the screens referred to above. Preferably the therapeutic agent is a chemical molecule of relatively low molecular weight, for example, less than about 1000. Examples of suitable classes of molecule include staurosporine analogues, tyrhostins and flavenoids. The therapeutic agent can also be peptide or an antisense mRNA encoding the protein tyrosine kinase.

The invention also extends to an enzyme-substrate complex which comprises a protein tyrosine kinase characterised by the amino acid sequence shown in SEQ ID NO. 2 or by an amino acid sequence showing a degree of homology thereto as defined above and a therapeutic agent capable of modulating the activity of the said protein tyrosine kinase.

The novel protein tyrosine kinase can also be used in prognostic and diagnostic applications Thus antibodies raised against the protein tyrosine kinase or nucleic acid encoding the novel tyrosine kinase can be used as the basis for screening tissue, in particular tumour tissue, for the presence of the novel protein tyrosine kinases. If, as in the case of c-erbB-2, the expression of the tyrosine kinase correlates with poor prognosis, then treatment of the patient could be modified accordingly.

Accordingly the present invention provides a method for detecting a tyrosine kinase having an amino acid sequence as defined in SEQ ID NO. 2 or a fragment thereof which comprises reacting a test sample with a specific antibody raised against an antigen from the said amino acid sequence and determining whether there is any antigen-antibody binding within the test sample. The test sample nay be for example a tissue sample, such as a tumour sample and presence of abnormal amounts of the protein tyrosine kinase may indicate development of or susceptibility to develop a tumour.

The invention also provides a method for detecting in a sample the presence of a nucleic acid species encoding a tyrosine kinase which method comprises subjecting the said sample or nucleic acid isolated therefrom to a procedure capable of detecting therein a defined nucleic acid sequence wherein said defined nucleic acid sequence comprises:

(a) all or part of the DNA sequence defined in SEQ ID No. 1, (b) DNA sequence from another part(s) of the tyrosine kinase characterised by the DNA sequence defined in (a); or (c) mRNA which would be the transcription product of such DNA.

Again presence of abnormal amounts of nucleic acid encoding the protein tyrosine kinase may indicate development of or susceptibility to develop a tumour.

Suitable methods for the detection of specific DNA sequences include Southern blotting and/or PCR using appropriate primers. Suitable methods for detecting mRNA include Northern blotting, RNAse protection studies and direct nucleic acid in situ hybridisation.

BRIEF DESCRIPTION OF THE DRAWINGS

Experimental work on which the invention is based is described in more detail in the following Example in which reference is made to the following figures in which:

FIG. 4 shows detection of brk mRNA expression in normal breast and grade III breast carcinoma tissue by RNase protection;

FIG. 5 shows detection of brk mRNA expression in normal breast and grade III breast carcinoma tissue by PCR.

EXAMPLE

Figure 1A:
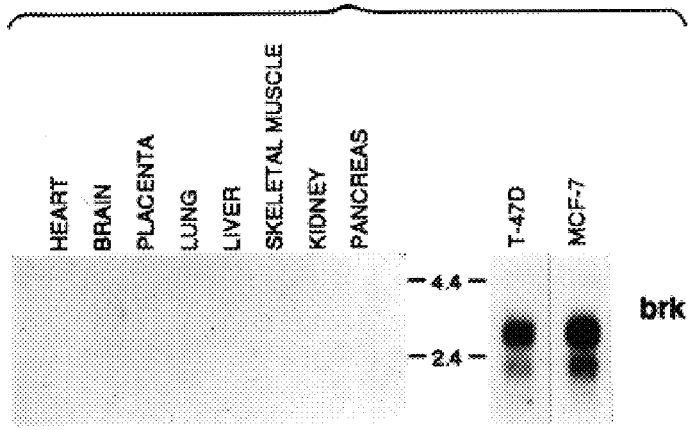
FIG. 1 shows expression of brk transcripts in human tissues and breast tumour cell lines.

Materials and Methods
Tissue Samples

Human lymph node and tumour samples were obtained from surgery and rapidly frozen in liquid nitrogen. Tumour grading was in accordance with accepted national criteria (Pathology Reporting in Breast Cancer Screening, Draft Guidance. Prepared by a Department of Health and Royal college of Pathologists Working Group (1989)) Breast Screening Publication ISBN 187997101. Normal breast tissue was obtained from reduction mammoplasty and rapidly frozen in liquid nitrogen. Frozen tissue samples were stored either in liquid nitrogen or at −70° C.

Cell Lines

Breast tumour cell lines were obtained from the American Type Culture Collection. Cell lines were maintained under conditions recommended by the supplier.

RNA Purification and Northern Hybridisation

Total RNA was purified from tissue samples using the method of Chomczynski and Sacchi (Anal. Biochem., 162, 156–159 (1987)). Cytoplasmic RNA was extracted from cell lines by the method of Wilkinson (Nuc. Acids. Res., 16, 10933 (1988)). Poly $A^+$ mRNA was purified using oligo dT spun columns (Pharmacia) according to manufacturer's instructions. RNA samples were electrophoresed through formaldehyde-agarose (1%) gels and transferred to Hybond N membranes (Amersham). The human tissue poly $A^+$ Northern blot was purchased from Clontech. $^{32}P$ radiolabelled probes were generated as previously described (Feinberg and Vogelstein, Anal. Biochem., 132 6–13 (1983)) and hybridised to membranes according to manufacturer's instructions. Membranes were washed at 65° C. at a final stringency of 0.1×SSC, 0.1% SDS.

Reverse Transcriptase-Polymerase Chain Reaction (RT-PCR), and PTK Differential Screen For the production of single stranded cDNA, 5 μg of RNA were digested with 7.5 units (u) RNase-free DNase I in 10 μl for 10 mins. at 37° C. in the presence of 40 u human placental RNase inhibitor. After extraction with phenol/chloroform and chloroform, the RNA was precipitated, resuspended in 10 μl water, denatured at 65° C. for 5 mins., and stored on ice. Reverse transcription reactions (10 μl) contained 2.5 μg RNA, 40 ng pdN6 (Pharmacia), 1 mM dNTPs, 40 u RNase inhibitor, 30 u AMV reverse transcriptase XL (Life Sciences Inc.) and reverse transcriptase buffer produced by the enzyme supplier. Control reactions contained no reverse transcriptase. Reactions were carried out at 41° C. for 1 hour.

Degenerate deoxyoligonucleotides were synthesised to amplify PTK encoding cDNA sequences.

SEQ ID NO. 3 (sense)
SEQ ID NO. 4 (antisense)

These primers are based on the following amino acid sequences

SEQ ID NO. 5
SEQ ID NO. 6 respectively.

Amplifications were carried out in 50 μl volumes containing 2 μl of single stranded cDNA, 60 mM KCl, 15 mM Tris-HCl (pH 8.8), 1.1 mM $MgCl_2$, 200 μM of each dNTP, 20 pmol of each primer and 2 u of Taq polymerase (Cetus). The PCR temperature cycle parameters were: 94° C. for 1 minute (min), 50° C. for 2 mins, 72° C. for 1 min, 30 cycles. For each RNA sample, control amplifications were performed on samples which had not subjected to reverse transcription (RT-controls).

The amplified PTK PCR products were electrophoresed through 3% agarose gels and purified using "Mermaid" reagents (Bio 101 inc). PCR products were subcloned into the vector pCR II (Invitrogen) according to supplier's instructions. Bacterial cell lysates from the involved node PTK fragment library were spotted on to duplicate Hybond N membranes. PTK PCR products amplified at higher levels from tumour bearing lymph nodes with respect to non-involved nodes were identified by differential DNA hybridisation using the protocol of Crompton et al, Nacl. Acids Res., 20, 4107–4108 (1992).

RT-PCR expression studies were carried out using specific primers based on the brk λt2 cDNA sequence (sense: 485–502, antisense: 1008–989) and the human glyceraldehyde 3-phosphate dehydrogenase (GAPDH) cDNA sequence (Arcari et al., Nacl. Acids Res., 12, 9179–9189 (1984)) (sense:71–96, antisense 1030–1053). Reverse transcription and PCR were carried out as described above, with all four primers in the same reaction. RT-controls were performed for each sample. After electrophoresis through 3% agarose gels, amplified GAPDH products were detected by ethidium bromide staining. Amplified brk products were detected by Southern transfer to Hybond-N membranes (Amersham) and probing with radiolabelled λt2 cDNA sequences (Sambrook et al., Molecular Cloning: A Laboratory Manual, Cold Spring Harbor Laboratory Press (1989)).

RACE PCR cDNA sequences 3' of the region amplified by the PTK PCR were isolated by a modification of the RACE protocols described by Frohman et al. (Proc. Natl. Acad. Sci. (USA), 85, 8998–9002 (1988)). T-47D RNA was reverse transcribed using a 'tagged' oligo dT primer as shown in

SEQ ID NO. 7.

Two specific sense oligodeoxynucleotides were used for the brk kinase sequence in consecutive PCR reactions. These were as shown in

SEQ ID NO. 8
SEQ ID NO. 9.

The reaction buffer was the same as described above except the $MgCl_2$ concentration was 1.5 mM. The PCR cycle parameters consisted of a single denaturation step at 92° C. for 2 mins, followed by 30 cycles at 92° C. for 1.25 mins, 56° C. for 2 mins and 72° C. for 2 mins.

5' RACE PCR was carried out using the Life Technologies 5' RACE system according to manufacturer's instructions. The two nested brk specific antisense oligodeoxynucleotides were as shown in

SEQ ID NO. 10

SEQ ID NO. 11.

The PCR cycle parameters consisted of a single denaturation step at 92° C. for 2 mins followed by 30 cycles at 92° C. for 1 min, 55° C. for 1.5 mins and 72° C. for 1.5 mins.

Constructions and Screening of cDNA Libraries

Cell line cDNA libraries were prepared in the vector lambda ZAPII (Stratagene) using reverse transcriptase (Superscript II, Life Technologies) and a uniZAP-cDNA synthesis kit (Stratagene). The complexities of the T-47D and MCF-7 libraries were $2.1 \times 10^6$ and $5 \times 10^6$. Libraries were screened using Hybond N nylon membranes (Amersham). $^{32}P$ radiolabelled DNA probes were hybridised to the membranes according to manufacturer's instructions. Filters were washed in 2×SSC, 0.1% SDS at 65° C. and finally in 0.1×SSC, 0.1% SDS at 65° C.

DNA Sequencing cDNA inserts were sequenced by the dideoxy method (Sanger et al., 1977) using the Sequenase version 2 sequencing kit (United States Biochemicals) after generating exonuclease III nested deletions in the phagemids SK⁻ and KS⁺ (Stratagene) and rescuing single stranded templates as described by the supplier.

Baculoviral Expression of brk

The brk cDNA λt2 was subcloned into the baculovirus transfer vector pVL1392 (Invitrogen). This was co-transfected with BaculoGold (Pharmingen) viral DNA onto *Spodoitera fruciperda* (Sf21) insect cells and three days later the medium was used in an agarose plaque assay. Recombinant plaques containing brk were isolated, characterised, and used to generate high titre viral stocks (>$3 \times 10^8$ pfu/ml). Monolayer cultures of Sf-21 cells were subsequently infected at a multiplicity of infection of 5 pfu/cell and analysed after 48 hrs. Insect cell lysates were prepared as previously described (Page et al., J. Biol. Chem., 264, 19147–19154 (1989)).

Bacterial Expression of brk and Immunodetection

A SmaI-HindIII fragment from clone λt2, encoding amino acids 3–451, was cloned into the bacterial expression plasmid pGEX-4T-3 (Pharmacia). Bacterial cultures expressing this plasmid were grown at 37° C. in L-broth containing 100 µg/ml ampicillin and induced with 0.1 mM isopropyl-β-D-thiogalactopyranoside for 2 hours. Induced bacteria were lysed by boiling in SDS-PAGE sample buffer.

Cell lysates were separated on 10% SDS-polyacrylamide gels and transferred to nitrocellulose membranes. Membranes were blocked by incubation in phosphate-buffered saline (PBS) containing 5% (w/v) non-fat dried milk-protein, washed with PBS/0.05% Triton X100, and incubated with the anti-phosphotyrosine monoclonal antibody 4G10 (UBI) (2 ng/ml) in L15 medium (Gibco BRL) containing 10% (v/v) FCS. The antibody was detected using the ECL detection reagents (Amersham) as according to manufacturer's instructions. Construction of expression vectors for expression of brk in mammalian cells The brk cDNA λt2 was isolated from the cDNA library as a subclone between the EcoRI and XhoI sites of pBluescript SK (−) (Stratagene). The cDNA was excised by digestion with KpnI and BamHI, its ends were blunted, and it was subcloned into the SmaI site of pBluescript KS (+) (Stratagene). Ligation in one orientation produced a construct whereby digestion with HindIII produced a fragment carrying the full brk coding sequence. This HindIII fragment was ligated into either pRcCMV (Invitrogen) or pREP8 (Invitrogen), and in each case clones with the 'sense' orientation were selected.

Stable Transfection of Human Mammary Epithelial Cells

The mammary epithelial cell line HB4a has shown itself to be resistant to transfection and a modified calcium phosphate transfection technique was used specifically for these cells to ensure successful stable expression of the vector. This was achieved using an episomal vector to provide stable expression of the brk cDNA and uniquely demonstrate a transformed phenotype. Two parameters proved critical to achieving increased transfection efficiency:

1. Use of OPTIMEM, an α-MEM based medium (Gibco), for seeding and transfection. A special feature of this medium is reduced phenol red (a pH indicator dye which is present in all media) and it is believed that the dye may interfere with transfection of HB4a cells.

2. A specific coarseness of calcium phosphate-DNA complex achieved by mixing DNA and calcium chloride with immediate vortexing for a duration of six seconds. The cells were then exposed to the precipitate overnight, shocked with 15% glycerol for exactly 2.5 min and then returned to standard growth medium.

RNase Protection

A Pst I fragment of the λt2 brk cDNA (bases 302–607) was subcloned into the vector pBluescript (Stratagene). The pTRI-GAPDH vector, containing a 316 bp human glyceraldehyde 3-phosphate dehydrogenase cDNA fragment, was obtained from Ambion Inc. Radiolabelled antisense RNA probes were transcribed from linearised vectors using standard procedures (Sambrook et al., Molecular Cloning: A Laboratory Manual, Cold Spring Harbor Laboratory Press (1989)). Probe purification and RNase protection were carried out using protocols and reagents in the 'Ambion RPA II' kit. Protected fragments were resolved on DNA sequencing polyacrylamide/urea gels, and detected in dried gels by autoradiography.

Results

Isolation of PTK cDNAs Differentially Expressed in a Breast Tumour Metastasis

RNA was isolated from involved and non-involved axillary nodes removed from a patient with metastatic breast carcinoma. The RNA was subjected to reverse transcription-polymerase chain reaction (RT-PcR) using degenerate oligonucleotides corresponding to the highly conserved amino acid sequences present in subdomains VI (SEQ ID No. 5) and IX (SEQ ID NO. 6) of the PTK catalytic domain (Hanks et al., Science, 241, 42–52 (1988)). The pool of PTK cDNA fragments amplified from involved node RNA was subcloned to create a plasmid library of PTK cDNAs. Radiolabelled probes prepared from the two pools of PTK fragments amplified from the involved and non-involved node RNAs were used to screen duplicate platings of the PCR fragment library. Of 50 duplicate clones screened, 4 were found to hybridise preferentially to the probe prepared from the PTX cDNA fragment pool amplified from the involved node RNA. Sequencing of these clones identified three different cDNA fragments whose deduced amino acid sequences inferred that they encoded PTKs. One of the cDNA fragments (designated PTK23) encoded an amino acid sequence showing homology to members of the src PTK family blk, c-src and c-yes. Further characterisation of this novel putative PTK named brk (breast tumour kinase) is described herein.

Isolation of brk cDNAs

Initially, a 600 base pair (bp) brk cDNA fragment was generated by 3' RACE (rapid amplification of cDNA ends) PCR, using two specific nested oligonucleotides corresponding to the brk sequence between the two degenerate primers. This 3' RACE fragment was then used in expression studies to identify human breast tumour cell lines and normal tissues that expressed the brk transcript. Northern analysis using the 600 bp fragment on total RNA isolated from a range of human breast tumour cell lines (MCF-7, T-47D, MDA MB 468, 415, -157 and BT474, data not shown) did not detect any brk transcripts. Using the same fragment as a probe on Northern blots containing poly A⁺ selected RNA, two transcripts in the size range of 2.3 kb and 2.6–2.8 kb were detected in the two human breast tumour cell lines tested (T-47D and MCF-7).

Figure 1B:
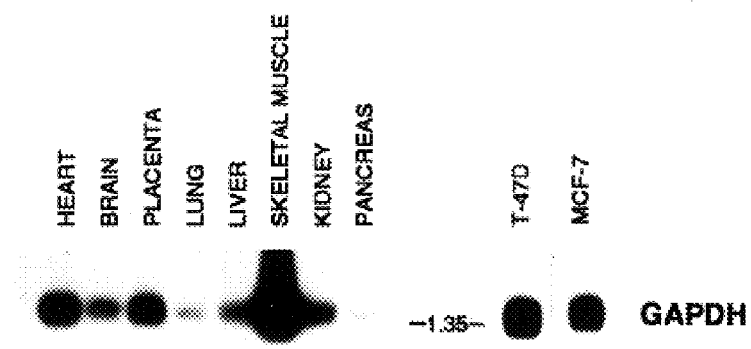

FIG. 1 shows expression of brk transcripts in human tissues and breast tumour cell lines. Northern blots, containing 2 μg of poly A⁺ RNA isolated from human tissues and two human breast tumour cell lines, were hybridised with a human brk probe (upper panel) and GAPDH probe (lower panel). The blots subjected to autoradiography for 10 days (brk) and 36 hours (GAPDH). The mobilities of the molecular weight markers are indicated in kb.

Subsequently, the 600 bp fragment was used to screen an unamplified cDNA library prepared from the T-47D cell line. From a screen of 1×10⁶ phage clones, two brk cDNAs were isolated, both of which contained inserts of approximately 2.5 kb.

Figure 2:
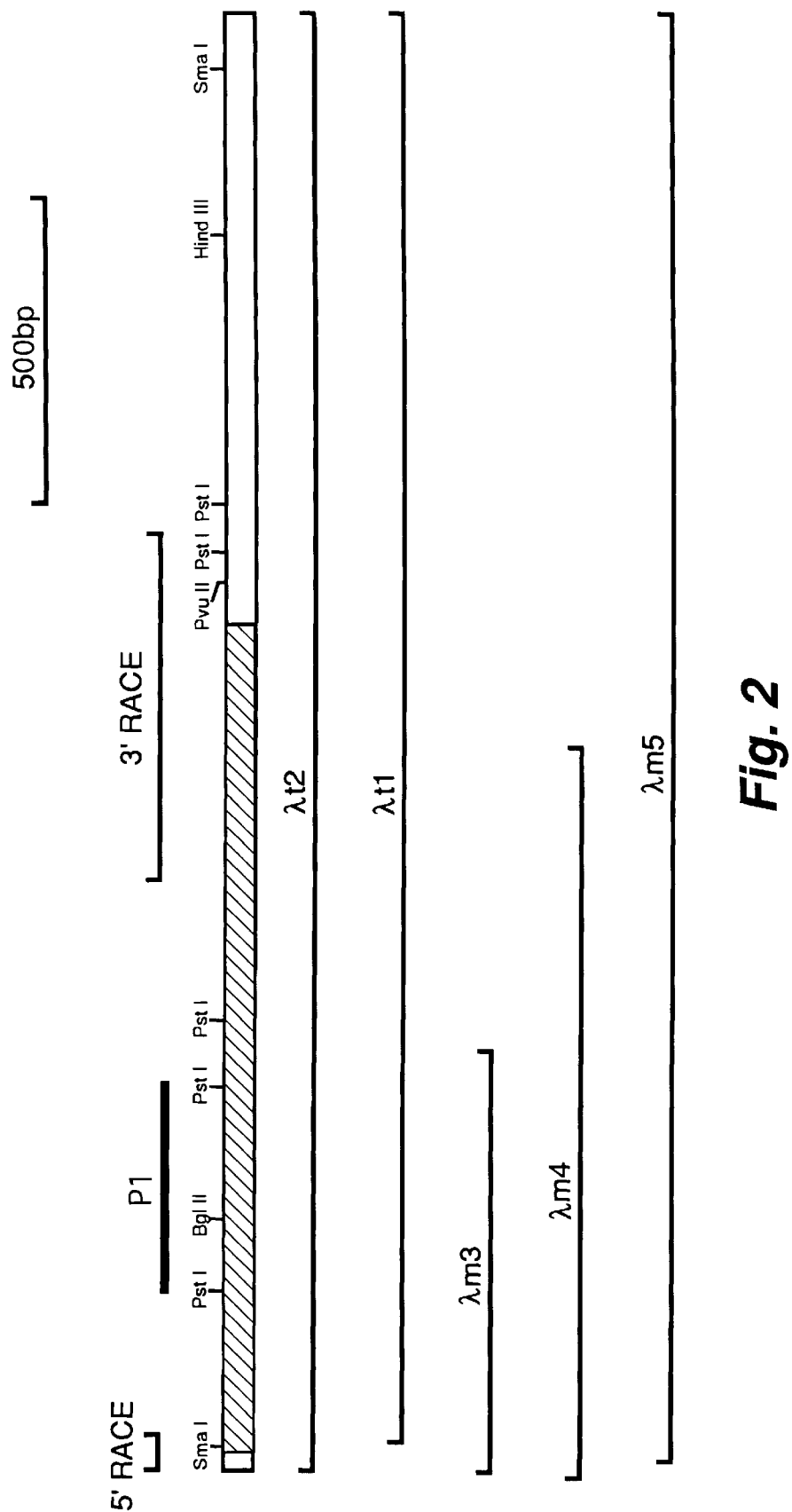
FIG. 2 shows a schematic representation of the human brk cDNA.

FIG. 2 shows a schematic representation of the human brk cDNA showing selected restriction sites, the relative positions of the end of the cDNA clones (λt1,2 and λm3–5) and the positions of the 5' and 3' RACE-PCR generated fragments. The shaded region represents the open reading frame present in clone λt2. P1 represents the 0.3 kb PstI-PstI fragment used in the RNase protection assay.

Sequencing of the slightly longer clone λt2 identified an open reading frame (ORF) of 1353 bp starting with a consensus sequence for efficient translational initiation (Kozak, J. Cell. Biol., 108, 229–241, (1989)) and terminating with a TGA codon at position 1392. The ORF was preceded by a 5' sequence of 28 bp that did not contain any in-frame stop codons.

The possibility arose that the cDNA clone λt2 did not contain the complete brk coding region. In order to identify potentially longer cDNAs, a radiolabelled restriction fragment corresponding to the 5' end of clone λt2 was used as a probe to screen 1×10⁶ phage clones from a MCF-7 cell line unamplified cDNA library. From this screen three cDNAs (λm 3–5) were isolated (FIG. 2), one of which (λm4) had an additional 17 bp of 5' sequence. No initiation or stop codons in frame with the ORF were identified in this upstream sequence. In addition to these studies, 5' RACE PCR was carried out using nested oligonucleotide primers, corresponding to the 5' end of clone λt2, on poly A⁺ RNA isolated from T-47D and MCF-7 cell lines. Subcloning and sequencing of the amplified products indicated that no more upstream sequence had been isolated (FIG. 2). Expression of clone λt2, by recombinant baculovirus infection of Sf21 cells, resulted in the synthesis of a protein whose mobility on SDS-polyacrylamide gels was consistent with the predicted molecular weight of the protein encoded by the ORF present.

Figures 3A, 3B, 3C:
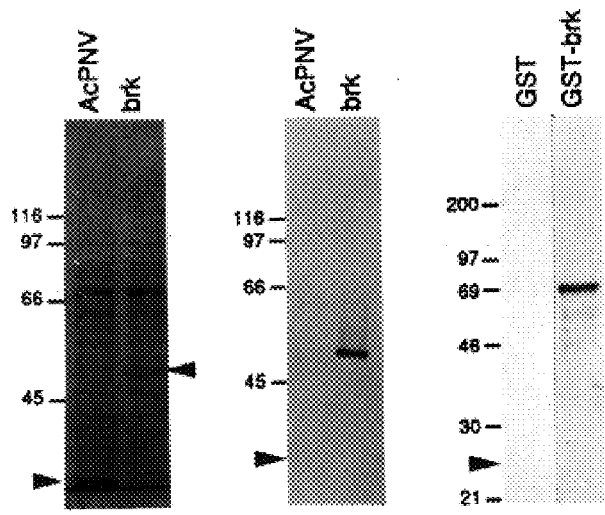
FIG. 3 shows baculovirus and bacterial protein expression of brk.

FIG. 3 shows baculoviral and bacterial protein expression of brk. Lysates from insect cells infected with wild type baculovirus (AcPNV) and a recombinant baculovirus containing the brk cDNA λt2 were subjected to SDS-PAGE (panel A). Proteins were visualised by staining with Coomassie blue G-250. Arrows indicate the positions of the wild type polyhedrin protein and the recombinant brk protein. The same insect cell lysates (panel B) and lysates from bacteria containing plasmids expressing GST or GST-brk fusion proteins (panel C) were subjected to SDS-PAGE and transferred to nylon membranes. Phosphotyrosine containing proteins were detected using the antibody 4G10. Duplicate membranes were incubated with only the detection reagents to confirm that detection was dependant on the 4G10 antibody. The arrows indicate the positions of polyhedrin (panel B) and GST proteins (panel C), as determined by Ponceau S staining of the membranes. The mobilities of the molecular weight markers are indicated in kDa.

In addition, in vitro translation in rabbit reticulocyte lysates using transcripts generated from clone λt2 resulted in the synthesis of a single protein with the same mobility (data not shown). These experiments indicated that the predicted start codon in the brk cDNAs could act as an initiation site for translation and, therefore, that clone λt2 most likely contained the complete brk coding region.

brk Encodes a Novel Putative Non-Receptor Kinase

The 1353 bp open reading frame present in cDNA λt2 encodes a protein of 451 amino acids with a predicted molecular weight of 52 kDa. The complete nucleotide sequence and amino acid translation of λt2 are shown in SEQ ID NO. 1. The amino acid sequence between positions 197–432 of brk has several motifs found in other PTK catalytic domains (Hanks et al., Science, 241, 42–52 (1988)). The putative ATP-binding motif, GSGYFG (SEQ ID NO: 13), is at position 198–203, with a downstream lysine residue at 219. The putative autophosphorylation site in the catalytic domain is conserved at position 342. In brk the strong indicator sequence of PTK specificity in subdomain VI corresponds to DLAARN (SEQ ID NO: 14) (position 312–317). This motif is shared with abl, fps, csk and bpk(atk), but not with the src subfamily genes (DLRAAN) (SEQ ID NO: 15). Amino acid sequences similar to SH2 (78–169) and SN3 (15–68) domains are also present. The predicted amino terminal methionine of brk is followed by valine and residue 7 is alanine. brk therefore lacks the residues thought to be necessary for post-translational N-terminal myristoylation (Kaplan et al., Mol. Cell. Biol., 8, 2435–2441 (1988)). The short carboxyl terminus following the tyrosine kinase domain of brk contains a potential regulatory tyrosine (position 447) equivalent to tyrosine 527 of c-src, but it is found in a very different sequence context. The predicted amino-terminal region of brk, beyond the putative SH3 domain, is very short and is equivalent in length to that of csk (Nada et al, Nature, 351, 69–72 (1991); Partanen et al., Oncogene, 6, 2013–2018 (1991); Brauninger et al., Gene, 110, 205–211 (1992)).

Expression of brk in Human Tissues and Breast Tumour Cell Lines

As mentioned previously, brk transcripts were not detected when Northern blots containing total RNA isolated from a variety of breast tumour cell lines were screened with the 600 bp brk 3' RACE fragment. Two transcripts in the size range of 2.3 kb and 2.6–2.8 kb were detected on Northern blots containing poly A⁺ mRNA isolated from the breast tumour cell lines MCF-7 and T-47D. No brk transcripts were detected on Northern blots containing poly A+ mRNA isolated from normal human heart, placenta, brain, lung, liver, skeletal muscle, kidney and pancreas (FIG. 1).

Using RNase protection and RT-PCR assays, we examined the expression of brk in normal breast samples (reduction mammoplasty) and in grade III breast carcinomas. In the RNase protection assay, a 305 bp protected fragment of similar intensity to that detected in T-47D RNA was detected in one out of five grade III breast carcinoma RNAs but not in two normal breast samples.

FIG. 4 shows detection of brk mRNA expression in normal breast and grade III breast carcinoma tissue by RNase protection. Total RNA samples were isolated from yeast, T-47D cell line, two different normal human breast samples and five different grade III breast carcinomas. RNAs were hybridised with a brk radiolabelled antisense RNA derived from the P1 cDNA fragment (FIG. 2) or with an antisense GAPDH RNA probe. After RNase digestion and separation on a sequencing gel, products were detected by autoradiography for 4 days at −70° C.

FIG. 5 shows detection of brk mRNA expression in normal breast and grade III breast carcinoma tissue by PCR. Specific primers were used to simultaneously amplify brk and GAPDH sequences present in cDNA synthesised from normal breast (N) or grade III breast carcinoma (T) RNAs. Products were resolved on agarose gels, and the amplified GAPDH products were visualised with ethidium bromide (lower portion of each panel). After transfer to nylon membranes, brk products were detected by probing with a specific radiolabelled cDNA and autoradiography (upper portion of each panel). Lanes immediately to the left of the visualised GAPDH sequences contain the products of amplification from the corresponding non-reverse-transcribed RNAs. The upper panel corresponds to the same RNA samples as shown in FIG. 4, excepting the left hand 'normal' sample in FIG. 4 which is omitted here. The two lower panels represent an additional 4 normal and 7 tumour samples.

By RT-PCR, a 600 bp reverse transcriptase-dependent brk product was specifically amplified from the tumour RNA which gave a positive signal in the RNase protection assay, when the same tumour and normal breast RNAs were analysed (FIG. 5, upper panel). Analysis of further normal breast and grade III breast carcinoma RNAs by RT-PCR detected another three out of seven tumours that expressed brk transcripts, whereas no brk products were amplified from four normal breast RNA samples (FIG. 5, lower panels).

Baculoviral and Bacterial Expression of brk cDNA

A recombinant baculovirus was generated containing the entire λt2 cDNA under the control of the polyhedrin promoter. Infected insect cells expressed a novel protein with an SDS-PAGE mobility of approximately 50 kDa (FIG. 3, A), consistent with the predicted molecular weight of 52 kDa. A bacterial vector was constructed to express the entire brk open reading frame, except for the first two N-terminal amino acids, as a glutathione S-transferase (GST) fusion protein. Cell lysates from bacterial cultures containing the GST-brk vector expressed an approximately 70 kDa fusion protein.

Western blots of both insect and bacterial cell lysates using an anti-phosphotyrosine antibody demonstrated that the baculovirally expressed 50 kDa protein and the bacterially expressed 70 kDa fusion protein were the major immunoreactive polypeptides present (FIG. 3). No immunoreactive polypeptides were present in insect cell lysates infected with a wild type baculovirus and cell lysates from bacteria expressing GST alone (FIG. 3).

Expression and Function of brk cDNAs in Mammalian Cells

N1H3T3 (clone b2B) cells were transfected either with pRcCMV or its derivative carrying the brk cDNA. The cells were selected with 1 mg/ml Geneticin, and clones of drug resistant cells were pooled. These populations were seeded at either $1 \times 10^4$ or $1 \times 10^5$ per well of a six well dish in 0.4% agar, and left for six weeks. At the end of this period, 20–30 μm colonies were observed with the cells containing the transfected brk cDNA, whereas none were observed with the cells transfected with the empty vector. In multiple seedings of $1 \times 10^4$ 'brk' cells, the numbers of colonies obtained were 44, 54 and 0; in the $1 \times 10^5$ seedings there were 81, 41, 50 and 42 colonies. Of 55 of these colonies, 32 were successfully isolated and grown on, whereas none of the cell aggregates picked from the 'vector only' cells in agar were capable of further proliferation. Seven of the expanded 'brk' clones were chosen at random and placed back in soft agar; five of these produced 50 μm colonies with 100% efficiency within seven days when seeded at $1 \times 10^4$ (lower efficiencies were observed at higher seeding densities). These data indicate that brk expression in N1H3T3 cells results in anchorage independent proliferation, a feature of neoplastically transformed cells. The clones of brk transformed N1H3T3 cells will be useful tools for the study of brk function, and for screening potential brk inhibitors.

HB4a, a conditionally immortalised human breast lumenal cell line (developed by Dr. M. O'Hare), was transfected with pREP8 or its derivative containing the brk cDNA, and transfectants were selected in 1 mM histidinol. For each plasmid, 50–60 drug resistant colonies were pooled and maintained under selection. The cells were seeded at $1 \times 10^5$ in duplicate in 0.4% agar and left for six weeks. The brk transfected cells produced an average of 373 50 μm clones, whereas the empty vector cells produced an average of 108. Thus, brk expression in these cells enhances their capacity to proliferate in an anchorage independent manner.

An Alternative brk cDNA

Sequencing of brk cDNA clone λm5 revealed a deletion corresponding to nucleotides 259 to 380 inclusive of SEQ ID NO. 1. The predicted protein product is identical to that in SEQ ID NO. 2 from the N-terminus up to and including residue 77. Following the deletion, the nucleotide sequence continues to correspond to that shown in SEQ ID NO. 1 (nucleotides 381 onwards) but with the reading frame changed so that the amino acid sequence diverges. The ensuing predicted amino acid sequence is shown in SEQ ID NO. 12 which is followed by a stop codon.

This protein would, therefore, comprise an SH3 domain identical in sequence to that of brk, but lack the SH2 and catalytic domains. Since SH3 domains may mediate protein-protein interactions, this protein may regulate brk function by competing for binding to specific protein partners.

What is claimed is:

1. A DNA isolate encoding a protein having a catalytic domain, said protein comprising an amino acid sequence as shown in SEQ ID NO:2, wherein said protein
catalyzes the transfer of phosphate groups from donor molecules to hydroxyl groups of tyrosine residues in polypeptides; and
is overexpressed in at least one human breast tumor as compared to normal breast tissue.

2. A DNA isolate according to claim 1 which has the DNA sequence shown in SEQ ID NO:1.

3. A recombinant expression vector comprising DNA according to claim 1 under control of an appropriate promoter and regulatory elements for expression in a host cell.

4. A recombinant cell line transformed with an expression vector according to claim 3 and capable of expressing said protein.

5. A recombinant cell line according to claim 4 which is a CHO, myeloma, primary immortalized breast, rodent fibroblast, baculovirus, yeast or *E. coli* cell line.

6. A DNA isolate encoding a protein comprising amino acids 1 to 77 of SEQ ID NO:2 directly linked to amino acids 1 to 57 of SEQ ID NO:12.

7. A DNA isolate encoding a protein fragment, said fragment containing at least the catalytic domain of the protein having the amino acid sequence as shown in SEQ ID NO:2, wherein said protein
catalyzes the transfer of phosphate groups from donor molecules to hydroxyl groups of tyrosine residues in polypeptides; and
is overexpressed in at least one human breast tumor as compared to normal breast tissue;
and wherein said protein fragment
comprises an epitope that reacts with antibodies raised against said protein; or
itself catalyzes the transfer of phosphate groups from donor molecules to hydroxyl groups of tyrosine residues in polypeptides.

8. A recombinant expression vector comprising DNA according to claim 7 under control of an appropriate promoter and regulatory elements for expression in a host cell.

9. A recombinant cell line transformed with an expression vector according to claim 8 and capable of expressing said fragment.

10. A recombinant cell line according to claim 9 which is a CHO, myeloma, primary immortalized breast, rodent fibroblast, baculovirus, yeast or *E. coli* cell line.

11. An isolated protein having a catalytic domain, said protein comprising an amino acid sequence as shown in SEQ ID NO:2, wherein said protein
catalyzes the transfer of phosphate groups from donor molecules to hydroxyl groups of tyrosine residues in polypeptides; and
is overexpressed in at least one human breast tumor as compared to normal breast tissue.

12. A protein according to claim 11 which has been produced recombinantly in a cell line.

13. A protein according to claim 12 which has been produced in a human tumor cell line.

14. An isolated protein comprising amino acids 1 to 77 of SEQ ID NO:2 directly linked to amino acids 1–57 of SEQ ID NO:12.

15. A protein fragment containing at least the catalytic domain of the protein having an amino acid sequence as shown in SEQ ID NO:2, wherein said protein
catalyzes the transfer of phosphate groups from donor molecules to hydroxyl groups of tyrosine residues in polypeptides; and
is overexpressed in at least one human breast tumor as compared to normal breast tissue;
and wherein said protein fragment:
(a) includes at least one epitope that reacts with antibodies raised against said protein; or
(b) itself catalyzes the transfer of phosphate groups from donor molecules to hydroxyl groups of tyrosine residues in polypeptides.

16. An isolated complex which comprises a protein having a catalytic domain, said protein comprising an amino acid sequence as shown in SEQ ID NO:2, wherein said protein
catalyzes the transfer of phosphate groups from donor molecules to hydroxyl groups of tyrosine residues in polypeptides; and
is overexpressed in at least one human breast tumor as compared to normal breast tissue;
and a therapeutic agent that impairs or inhibits the activity of said protein in catalyzing transfer of Phosphate groups from donor molecules to hydroxyl groups of tyrosine residues in polypeptides or that impairs or inhibits the activity of said protein as a signaling molecule.

17. A complex according to claim 16 wherein said therapeutic agent is a chemical molecule, with a molecular weight of about 1000 or less.

18. A complex according to claim 17 wherein said therapeutic agent is a staurosporine analogue, a tyrphostin or a flavenoid.

19. A complex according to claim 16 wherein said therapeutic agent is an antibody.

20. A complex according to claim 16 wherein said therapeutic agent is a peptide.

21. A isolated complex which comprises a protein fragment containing at least the catalytic domain of the protein having an amino acid sequence as shown in SEQ ID NO:2, wherein said protein catalyzes the transfer of phosphate groups from donor molecules to hydroxyl groups of tyrosine residues in polypeptides; and is overexpressed in at least one human breast tumor as compared to normal breast tissue;

and wherein said protein fragment catalyzes the transfer of phosphate groups from donor molecules to hydroxyl groups of tyrosine residues in polypeptides, and a therapeutic agent that is capable of impairing or inhibiting the activity of said protein fragment in catalyzing transfer of phosphate groups from donor molecules to hydroxyl groups of tyrosine residues in polypeptides or that is capable of impairing or inhibiting the activity of said protein as a signaling molecule.

22. A complex according to claim 21 wherein said therapeutic agent is a chemical molecule with a molecular weight of about 1000 or less.

23. A complex according to claim 22 wherein said therapeutic agent is a staurosporine analogue, a tyrphostin or a flavenoid.

24. A complex according to claim 21 wherein said therapeutic agent is an antibody.

25. A complex according to claim 21 wherein said therapeutic agent is a peptide.

* * * * *

UNITED STATES PATENT AND TRADEMARK OFFICE
CERTIFICATE OF CORRECTION

PATENT NO. : 6,051,221
DATED : April 18, 2000
INVENTOR(S) : Gusterson et al.

It is certified that error appears in the above-identified patent and that said Letters Patent is hereby corrected as shown below:

Title page,
Item [73], Assignee, change "Glaxo Wellcome Inc., Research Triangle Park, N.C." to read as -- The Institute of Cancer Research, Sutton, Surrey, Great Britain; Glaxo Wellcome Inc., Research Triangle Park, N.C. --

Signed and Sealed this

First Day of February, 2005

JON W. DUDAS
*Director of the United States Patent and Trademark Office*

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
      (A) LENGTH: 2507 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 29..1381

(xi) SEQUENCE DESCRIPTION: SEQ ID NO: 1:

```
CCTGGTCCTG CCGCTGCGCC CGCCCGCC ATG GTG TCC CGG GAC CAG GCT CAC        52
                              Met Val Ser Arg Asp Gln Ala His
                                1               5

CTG GGC CCC AAG TAT GTG GGC CTC TGG GAC TTC AAG TCC CGG ACG GAC      100
Leu Gly Pro Lys Tyr Val Gly Leu Trp Asp Phe Lys Ser Arg Thr Asp
     10              15                  20

GAG GAG CTG AGC TTC CGC GCG GGG GAC GTC TTC CAC GTG GCC AGG AAG      148
Glu Glu Leu Ser Phe Arg Ala Gly Asp Val Phe His Val Ala Arg Lys
 25              30                  35                  40

GAG GAG CAG TGG TGG TGG GCC ACG CTG CTG GAC GAG GCG GGT GGG GCC      196
Glu Glu Gln Trp Trp Trp Ala Thr Leu Leu Asp Glu Ala Gly Gly Ala
                 45                  50                  55

GTG GCC CAG GGC TAT GTG CCC CAC AAC TAC CTG GCC GAG AGG GAG ACG      244
Val Ala Gln Gly Tyr Val Pro His Asn Tyr Leu Ala Glu Arg Glu Thr
             60                  65                  70

GTG GAG TCG GAA CCG TGG TTC TTT GGC TGC ATC TCC CGC TCG GAA GCT      292
Val Glu Ser Glu Pro Trp Phe Phe Gly Cys Ile Ser Arg Ser Glu Ala
         75                  80                  85

GTG CGT CGG CTG CAG GCC GAG GGC AAC GCC ACG GGC GCC TTC CTG ATC      340
Val Arg Arg Leu Gln Ala Glu Gly Asn Ala Thr Gly Ala Phe Leu Ile
     90                  95                 100

AGG GTC AGC GAG AAG CCG AGT GCC GAC TAC GTC CTG TCG GTG CGG GAC      388
Arg Val Ser Glu Lys Pro Ser Ala Asp Tyr Val Leu Ser Val Arg Asp
105                 110                 115                 120

ACG CAG GCT GTG CGG CAC TAC AAG ATC TGG CGG CGT GCC GGG GGC CGG      436
Thr Gln Ala Val Arg His Tyr Lys Ile Trp Arg Arg Ala Gly Gly Arg
                125                 130                 135

CTG CAC CTG AAC GAG GCG GTG TCC TTC CTC AGC CTG CCC GAG CTT GTG      484
Leu His Leu Asn Glu Ala Val Ser Phe Leu Ser Leu Pro Glu Leu Val
            140                 145                 150

AAC TAC CAC AGG GCC CAG AGC CTG TCC CAC GGC CTG CGG CTG GCC GCG      532
Asn Tyr His Arg Ala Gln Ser Leu Ser His Gly Leu Arg Leu Ala Ala
        155                 160                 165

CCC TGC CGG AAG CAC GAG CCT GAG CCC CTG CCC CAT TGG GAT GAC TGG      580
Pro Cys Arg Lys His Glu Pro Glu Pro Leu Pro His Trp Asp Asp Trp
    170                 175                 180

GAG AGG CCG AGG GAG GAG TTC ACG CTC TGC AGG AAG CTG GGG TCC GGC      628
Glu Arg Pro Arg Glu Glu Phe Thr Leu Cys Arg Lys Leu Gly Ser Gly
185                 190                 195                 200

TAC TTT GGG GAG GTC TTC GAG GGG CTC TGG AAA GAC CGG GTC CAG GTG      676
Tyr Phe Gly Glu Val Phe Glu Gly Leu Trp Lys Asp Arg Val Gln Val
                205                 210                 215
```

```
GCC ATT AAG GTG ATT TCT CGA GAC AAC CTC CTG CAC CAG CAG ATG CTG      724
Ala Ile Lys Val Ile Ser Arg Asp Asn Leu Leu His Gln Gln Met Leu
            220                 225                 230

CAG TCG GAG ATC CAG GCC ATG AAG AAG CTG CGG CAC AAA CAC ATC CTG      772
Gln Ser Glu Ile Gln Ala Met Lys Lys Leu Arg His Lys His Ile Leu
        235                 240                 245

GCG CTG TAC GCC GTG GTG TCC GTG GGG GAC CCC GTG TAC ATC ATC ACG      820
Ala Leu Tyr Ala Val Val Ser Val Gly Asp Pro Val Tyr Ile Ile Thr
    250                 255                 260

GAG CTC ATG GCC AAG GGC AGC CTG CTG GAG CTG CTC CGC GAC TCT GAT      868
Glu Leu Met Ala Lys Gly Ser Leu Leu Glu Leu Leu Arg Asp Ser Asp
265                 270                 275                 280

GAG AAA GTC CTG CCC GTT TCG GAG CTG CTG GAC ATC GCC TGG CAG GTG      916
Glu Lys Val Leu Pro Val Ser Glu Leu Leu Asp Ile Ala Trp Gln Val
                285                 290                 295

GCT GAG GGC ATG TGT TAC CTG GAG TCG CAG AAT TAC ATC CAC CGG GAC      964
Ala Glu Gly Met Cys Tyr Leu Glu Ser Gln Asn Tyr Ile His Arg Asp
                300                 305                 310

CTG GCC GCC AGG AAC ATC CTC GTC GGG GAA AAC ACC CTC TGC AAA GTT     1012
Leu Ala Ala Arg Asn Ile Leu Val Gly Glu Asn Thr Leu Cys Lys Val
            315                 320                 325

GGG GAC TTC GGG TTA GCC AGG CTT ATC AAG GAG GAC GTC TAC CTC TCC     1060
Gly Asp Phe Gly Leu Ala Arg Leu Ile Lys Glu Asp Val Tyr Leu Ser
        330                 335                 340

CAT GAC CAC AAT ATC CCC TAC AAG TGG ACG GCC CCT GAA GCG CTC TCC     1108
His Asp His Asn Ile Pro Tyr Lys Trp Thr Ala Pro Glu Ala Leu Ser
345                 350                 355                 360

CGA GGC CAT TAC TCC ACC AAA TCC GAC GTC TGG TCC TTT GGG ATT CTC     1156
Arg Gly His Tyr Ser Thr Lys Ser Asp Val Trp Ser Phe Gly Ile Leu
                365                 370                 375

CTG CAT GAG ATG TTC AGC AGG GGT CAG GTG CCC TAC CCA GGC ATG TCC     1204
Leu His Glu Met Phe Ser Arg Gly Gln Val Pro Tyr Pro Gly Met Ser
                380                 385                 390

AAC CAT GAG GCC TTC CTG AGG GTG GAC GCC GGC TAC CGC ATG CCC TGC     1252
Asn His Glu Ala Phe Leu Arg Val Asp Ala Gly Tyr Arg Met Pro Cys
            395                 400                 405

CCT CTG GAG TGC CCG CCC AGC GTG CAC AAG CTG ATG CTG ACA TGC TGG     1300
Pro Leu Glu Cys Pro Pro Ser Val His Lys Leu Met Leu Thr Cys Trp
        410                 415                 420

TGC AGG GAC CCC GAG CAG AGA CCC TGC TTC AAG GCC CTG CGG GAG AGG     1348
Cys Arg Asp Pro Glu Gln Arg Pro Cys Phe Lys Ala Leu Arg Glu Arg
425                 430                 435                 440

CTC TCC AGC TTC ACC AGC TAC GAG AAC CCG ACC TGAGCTGCTG TGGAGCGGGC   1401
Leu Ser Ser Phe Thr Ser Tyr Glu Asn Pro Thr
                445                 450

ATGGCCGGGC CCTGCTGAGG AGGGGCCTGG GCAGAGGGCC TGGACCTGGG ATCAAGGCCC   1461

ACGCGCTTCC CTGGGGTTTA CTGAGGTGAT GGGTGCAGGA AAGGTTCACA AATGTGGAGT   1521

GTCTGCGTCC AATACACGCG TGTGCTCCTC TCCTTACTCC ATCGTGTGTG CCTTGGGTCT   1581

CAGCTGCTGA CACGCAGCCT GCTCTGGAGC CTGCAGATGA GATCCGGGAG ACTGACACGA   1641

AGCCAGCAGA GGTCAGAGGG GACTCTGACC ACAGCCCGCT CTCTGGCTGT CTGTCTGCAG   1701

TGCCCGGCTG AGGGTGGGAG GCAAACACGC CTTGTTCCTG CTCTTCCCAG TTCAGCTTGG   1761

TGGGAGAAAG TCATTCGCGT GGCTCGGGAC GCTCATGTAA ATTTGGTTTT GGTGCTCAAG   1821

GGTTCTTTCC TCCCAGGGGC AGGTGTTTCT TTCCTGTTTG TCTTGTGTCT TGAGAGCTTG   1881

GCCTTATGAC CAGTGAGAAC TCTCTCCCTG GTCTCTGCCA GCCCAAGCAT CACTGCCCGA   1941
```

-continued

```
GGCGCCAGCT CAGTTTCACC GTCCACGTCC ACAAGGGGCT TTTCCCACCT TCACCTTTGT    2001

CGCTGGGTCA GTGCTGGAAA GCGCCCCTCA CTCCTGCGCT GACAAGGGCC CTTCTCTACT    2061

GTCTGTGGGG TGGTTCCGGG CTGGGGGGGC TGCCTCCTTT GCACCTGATT TTGAAGGTGT    2121

CTCTTTCATC CATGGTTAAG TCATAAAAAG CTTATTGGTT TTGGTTTTGA CTCACCTGAA    2181

AGTTTTTTTG GTTTAAAAGA AGAATAGGCG GGGCACGGTG GCTCGTGCCT GTAATCCCAG    2241

CACTTTGGGA GGCTGAGGCA GGTGGATCAC GAGGTCAGGA GATCGACACC ATCCTGGCTA    2301

ACACGGTGAA GCCCCGTCTC TACTAAAAAA TACAAAAAAT TAGCTGGGTG TGGTGGTGGG    2361

GGTGGGCGCC TGTGGTCCCA GCTACGTGGG AGGCTGAGGC AGCAGACTGG TGTGAACCCG    2421

GGAGGTGGAG CTTGCAGTGA GCCGAGGTCG CGCCACTGCA CTCCAGCCTG GGCGACAGAG    2481

CGAGACTCCA TCTCAAAAAA AAAAAA                                         2507
```

(2) INFORMATION FOR SEQ ID NO: 2:

(i) SEQUENCE CHARACTERISTICS:
        (A) LENGTH: 451 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Val Ser Arg Asp Gln Ala His Leu Gly Pro Lys Tyr Val Gly Leu
 1               5                  10                  15

Trp Asp Phe Lys Ser Arg Thr Asp Glu Glu Leu Ser Phe Arg Ala Gly
            20                  25                  30

Asp Val Phe His Val Ala Arg Lys Glu Glu Gln Trp Trp Trp Ala Thr
        35                  40                  45

Leu Leu Asp Glu Ala Gly Gly Ala Val Ala Gln Gly Tyr Val Pro His
    50                  55                  60

Asn Tyr Leu Ala Glu Arg Glu Thr Val Glu Ser Glu Pro Trp Phe Phe
 65                 70                  75                  80

Gly Cys Ile Ser Arg Ser Glu Ala Val Arg Arg Leu Gln Ala Glu Gly
                85                  90                  95

Asn Ala Thr Gly Ala Phe Leu Ile Arg Val Ser Glu Lys Pro Ser Ala
           100                 105                 110

Asp Tyr Val Leu Ser Val Arg Asp Thr Gln Ala Val Arg His Tyr Lys
       115                 120                 125

Ile Trp Arg Arg Ala Gly Gly Arg Leu His Leu Asn Glu Ala Val Ser
   130                 135                 140

Phe Leu Ser Leu Pro Glu Leu Val Asn Tyr His Arg Ala Gln Ser Leu
145                 150                 155                 160

Ser His Gly Leu Arg Leu Ala Ala Pro Cys Arg Lys His Glu Pro Glu
               165                 170                 175

Pro Leu Pro His Trp Asp Asp Trp Glu Arg Pro Arg Glu Glu Phe Thr
           180                 185                 190

Leu Cys Arg Lys Leu Gly Ser Gly Tyr Phe Gly Glu Val Phe Glu Gly
       195                 200                 205

Leu Trp Lys Asp Arg Val Gln Val Ala Ile Lys Val Ile Ser Arg Asp
   210                 215                 220

Asn Leu Leu His Gln Gln Met Leu Gln Ser Glu Ile Gln Ala Met Lys
225                 230                 235                 240

Lys Leu Arg His Lys His Ile Leu Ala Leu Tyr Ala Val Val Ser Val
               245                 250                 255
```

```
Gly Asp Pro Val Tyr Ile Ile Thr Glu Leu Met Ala Lys Gly Ser Leu
            260                 265                 270

Leu Glu Leu Leu Arg Asp Ser Asp Glu Lys Val Leu Pro Val Ser Glu
            275                 280                 285

Leu Leu Asp Ile Ala Trp Gln Val Ala Glu Gly Met Cys Tyr Leu Glu
            290                 295                 300

Ser Gln Asn Tyr Ile His Arg Asp Leu Ala Ala Arg Asn Ile Leu Val
305                 310                 315                 320

Gly Glu Asn Thr Leu Cys Lys Val Gly Asp Phe Gly Leu Ala Arg Leu
                325                 330                 335

Ile Lys Glu Asp Val Tyr Leu Ser His Asp His Asn Ile Pro Tyr Lys
            340                 345                 350

Trp Thr Ala Pro Glu Ala Leu Ser Arg Gly His Tyr Ser Thr Lys Ser
            355                 360                 365

Asp Val Trp Ser Phe Gly Ile Leu Leu His Glu Met Phe Ser Arg Gly
            370                 375                 380

Gln Val Pro Tyr Pro Gly Met Ser Asn His Glu Ala Phe Leu Arg Val
385                 390                 395                 400

Asp Ala Gly Tyr Arg Met Pro Cys Pro Leu Glu Cys Pro Pro Ser Val
                405                 410                 415

His Lys Leu Met Leu Thr Cys Trp Cys Arg Asp Pro Glu Gln Arg Pro
            420                 425                 430

Cys Phe Lys Ala Leu Arg Glu Arg Leu Ser Ser Phe Thr Ser Tyr Glu
            435                 440                 445

Asn Pro Thr
    450

(2) INFORMATION FOR SEQ ID NO: 3:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

GGAATTCTAG AMGSGACYTG GCVGCBAGRA AC                                32

(2) INFORMATION FOR SEQ ID NO: 4:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

GGAATTCTAG ACACSCCRWA RSWCCASACR TC                                32

(2) INFORMATION FOR SEQ ID NO: 5:

(i) SEQUENCE CHARACTERISTICS:
        (A) LENGTH: 8 amino acids
        (B) TYPE: amino acid
        (D) TOPOLOGY: linear (ii) MOLECULE TYPE: peptide
```

(xi) SEQUENCE DESCRIPTION: SEQ ID NO: 5:

His Arg Asp Leu Ala Ala Arg Asn
1               5

(2) INFORMATION FOR SEQ ID NO: 6:

(i) SEQUENCE CHARACTERISTICS:
          (A) LENGTH: 7 amino acids
          (B) TYPE: amino acid
          (D) TOPOLOGY: linear (ii) MOLECULE TYPE: peptide (ix) FEATURE:
          (A) NAME/KEY: Modified-site
          (B) LOCATION: 5
          (D) OTHER INFORMATION: /note= "Xaa at position 5 is Tyr or
               Phe"

(ix) FEATURE:
          (A) NAME/KEY: Modified-site
          (B) LOCATION: 7
          (D) OTHER INFORMATION: /note= "Xaa at position 7 is Val or
               Ile"

(xi) SEQUENCE DESCRIPTION: SEQ ID NO: 6:

Asp Val Trp Ser Xaa Gly Xaa
1               5

(2) INFORMATION FOR SEQ ID NO: 7:

(i) SEQUENCE CHARACTERISTICS:
          (A) LENGTH: 35 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 7:

GACTCGAGTC GACATCGATT TTTTTTTTTT TTTTT                          35

(2) INFORMATION FOR SEQ ID NO: 8:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 8:

CCTCGTCGGG GAAAACACC                                            19

(2) INFORMATION FOR SEQ ID NO: 9:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 9:

GGCTTATCAA GGAGGACGTC                                           20

(2) INFORMATION FOR SEQ ID NO: 10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

CTGGCCACGT GGAAGAC                                     17

(2) INFORMATION FOR SEQ ID NO: 11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

ACTTGAAGTC CCAGAGG                                     17

(2) INFORMATION FOR SEQ ID NO: 12:

(i) SEQUENCE CHARACTERISTICS:
        (A) LENGTH: 57 amino acids
        (B) TYPE: amino acid
        (D) TOPOLOGY: linear (ii) MOLECULE TYPE: peptide (xi) SEQUENCE DESCRIPTION: SEQ ID NO: 12:

```
Ala Gly His Ala Gly Cys Ala Ala Leu Gln Asp Leu Ala Ala Cys Arg
1               5                  10                  15

Gly Pro Ala Ala Pro Glu Arg Gly Gly Val Leu Pro Gln Pro Ala Arg
            20                  25                  30

Ala Cys Glu Leu Pro Gln Gly Pro Glu Pro Val Pro Arg Pro Ala Ala
        35                  40                  45

Gly Arg Ala Leu Pro Glu Ala Arg Ala
    50                  55
```

(2) INFORMATION FOR SEQ ID NO: 13:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 13:

```
Gly Ser Gly Tyr Phe Gly
1               5
```

(2) INFORMATION FOR SEQ ID NO: 14:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 14:

```
Asp Leu Ala Ala Arg Asn
1               5
```

(2) INFORMATION FOR SEQ ID NO: 15:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 15:

```
Asp Leu Arg Ala Ala Asn
1               5
```